United States Patent [19]

Badal et al.

[11] Patent Number: 5,457,030
[45] Date of Patent: Oct. 10, 1995

[54] METHOD AND COMPOSITION FOR DETERMINING ANTIMICROBIAL SUSCEPTIBILITY OF THE MAJORITY CLINICALLY SIGNIFICANT GRAM POSTITIVE ORGANISM

[75] Inventors: Robert Badal, Sacramento, Calif.; Roger Kelley, Kansas City, Mo.; Theodore T. Sand, Poway; Shoshana Bascomb, Davis, both of Calif.

[73] Assignee: MicroScan, Inc., West Sacramento, Calif.

[21] Appl. No.: 128,335

[22] Filed: Sep. 29, 1993

Related U.S. Application Data

[63] Continuation of Ser. No. 988,367, Dec. 9, 1992, abandoned, which is a continuation of Ser. No. 877,342, Apr. 29, 1992, abandoned, which is a continuation of Ser. No. 635,088, Dec. 28, 1990, abandoned.

[51] Int. Cl.$^6$ .............................. C12Q 1/04; C12Q 1/18
[52] U.S. Cl. .............................. 435/34; 435/29; 435/32; 435/968; 436/800
[58] Field of Search .............................. 435/29, 32, 34, 435/968; 436/800

[56] References Cited

U.S. PATENT DOCUMENTS

| | | | |
|---|---|---|---|
| 3,509,026 | 4/1970 | Sanders | 435/33 |
| 3,832,532 | 8/1974 | Praglin et al. | 364/413.9 |
| 3,957,583 | 5/1976 | Gibson | 435/34 |
| 4,025,393 | 5/1977 | Hirschfeld | 435/34 |
| 4,026,767 | 5/1977 | Shih | 435/34 |
| 4,030,980 | 6/1977 | Beckford et al. | 435/296 |
| 4,126,516 | 1/1978 | Missing | 435/34 |
| 4,129,483 | 12/1978 | Bochner | 435/34 |
| 4,236,211 | 11/1980 | Arvesen | 364/413.01 |
| 4,242,447 | 12/1980 | Findl et al. | 435/39 |
| 4,308,348 | 12/1981 | Monget | 435/38 |
| 4,568,637 | 2/1986 | Klein | 435/32 |
| 4,591,554 | 5/1986 | Koumura et al. | 435/18 |
| 4,603,108 | 7/1986 | Bascomb | 435/34 |
| 4,728,607 | 3/1988 | Dorn et al. | 435/34 |
| 4,812,393 | 3/1989 | Goswami | 435/4 |
| 4,812,409 | 3/1989 | Babb | 435/4 |
| 4,916,060 | 4/1990 | Weaver | 435/29 |
| 5,223,401 | 6/1993 | Faltz et al. | 435/18 |

FOREIGN PATENT DOCUMENTS

| | | |
|---|---|---|
| 0091837 | 10/1983 | European Pat. Off. |
| 0210417 | 2/1987 | European Pat. Off. |
| 0347771 | 6/1989 | European Pat. Off. |
| 2031949 | 4/1980 | United Kingdom |
| 8002295 | 10/1980 | WIPO |

OTHER PUBLICATIONS

Nolte et al J Clinical Microbiology vol. 26 pp. 1079–1084 (1968).
Staneck J Clinical Microbiology vol. 22 No. 2 pp. 187–191 (1989).
Staneck J Clinical Microbiology vol. 26 No. 1 pp. 1–7 (1988).
Barman, Leucine Aminopeptidase, Enzyme Handbook II:928 (1969).
Barry, Simple and Rapid Methods for Bacterial identifications, Clin. Lab. Med., 5:3–16 (1985).
Bascomb, Computers in Taxonomy and Systematics, Computers in Microbiology, 4:65–97 (1989).
Bobey et al., Rapid Detection of Yeast Enzymes by Using 4–Methylumbelliferyl Substrates, J. Clin. Micro. 13:393–394 (1981).
Cooper, Manual Clinical Microbiology (3rd Ed. E. Lennette 1980), Section v II. Fungi: chapter 52– Introduction to Clinical: 1.533–540.
Davenport, An Introduction to Yeasts and Yeast–like Organisms, Biology and Activities of Yeasts pp. 1–27 (1980).
Doern et al., Sensititre Autoreader for Same–Day Breakpoint Broth Microdilution Susceptibility Testing for Members of the Family Enterobacteriaceas, J. Clin. Micro. 25:1481–85 (1987).
Jones et al., An Electrophoretic Study of Enzymes as a Tool in the Taxonomy of the Dermatophytes, J. Gen'l. Micro. pp. 1101–1107 (1982).
Lee et al., Identification of Yeast Phase of Pathogenic Fungi by the Specificity of their Aminopeptidase(s), Sabouraudia 13:132–141 (1975).
Matteo et al., Rapid Microbial Enumeration with Aminopeptidase Substrates, Abstracts of Am. Soc. Microbiology, May 16, 1980, p. 308.
McGinnis, Yeast Identification, Lab. Handbook Med. Mycology 5:264, 337, 341,346, 395, 611 (1980).
McKie et al., Rapid Determination of Minimum Inhibitory Concentrations of Antimicrobial Agents by Regression Analysis of Light Scattering Data, Antimicro. Agents Chem. 17:813–23 (1980).
Nolte et al., Rapid and Overnight Microdilution Antibiotic Susceptibility Testing with the Sensititre Breakpoint Autoreader System, J. Clin. Micro. 26:1079–84 (1988).
Roman et al., Preliminary Investigation of Candida albicans Biovars, J. Clin. Micro. 18:430–431 (1983).
Silva–Hutner et al. I, Medically Important Yeasts, Manual of Clinical Microbiology (3rd Ed. E. Lennette 1980), chapter 56:491–507.
Silva–Hutner et al. II, Yeasts of Medical Importance Manual of Clinical Microbiology (3rd Ed. E. Lennetter 1980), 55:562–576.
Staneck et al. I, Automated Reading of MIC Microdilution Trays Containing Fluorogenic Enzyme Substrates with the Sensititre Autoreader, J. Clin. Micro. 22:187–191 (1985).
Staneck et al. II, Rapid MIC Testing with the Sensititre Autoreader, J. Clin. Micro. 26:1–7 (1988).
Urban, Rapid Determination of the Susceptibility of Bacteria to Antibiotics with 'Sensititre' Plates and Nitroblue Tetrazolium, J. Antimicrobial Chemo., 8:363–369 (1981).
Watson, Substrate Specificities of Aminopeptidases: A Specific Method for Microbial Differentiation, Methods in Micro., 9:1–14 (1976).

Primary Examiner—William H. Beisner
Assistant Examiner—Jane Williams
Attorney, Agent, or Firm—Cynthia G. Tymeson; Lois K. Winston; Mark J. Buonaiuto

[57] ABSTRACT

This invention relates to a method to determine susceptibility to antimicrobial agents of a majority of clinically significant Gram positive organisms. This invention also relates to a mixture of fluorogenic substrates used to detect the growth of Gram positive bacteria.

10 Claims, No Drawings

METHOD AND COMPOSITION FOR DETERMINING ANTIMICROBIAL SUSCEPTIBILITY OF THE MAJORITY CLINICALLY SIGNIFICANT GRAM POSTITIVE ORGANISM

This is a continuation of application Ser. No. 07/988,367, filed on Dec. 9, 1992, now abandoned, which is a continuation of application Ser. No. 07/877,342, filed on Apr. 29, 1992, now abandoned, which is a continuation of application Ser. No. 07/635,088, filed on Dec. 28, 1990, now abandoned.

FIELD OF THE INVENTION

This invention relates to a method to determine susceptibility to antimicrobial agents of a wide variety of clinically significant Gram positive organisms. This invention also relates to a mixture of fluorogenic substrates used to detect the growth of Gram positive bacteria.

BACKGROUND OF THE INVENTION

Microorganisms isolated from patients and other sources are routinely tested for their susceptibility to antimicrobial agents and for their metabolic growth requirements. In particular, the minimum inhibitory concentrations (MIC's) of antimicrobial agents or the categorical interpretations (susceptible, moderately susceptible, or resistant) of microorganisms isolated from clinical sources are routinely determined.

Numerous methods and apparatus have been developed to conduct susceptibility tests. In particular, multi-compartmentalized devices, such as microdilution panels, with each compartment containing a specific quantity of an antimicrobial agent or a growth promoting material, such as a vitamin, are often used to determine growth and susceptibilities. These compartments generally contain, in addition to the agent investigated, growth supporting medium. These devices may be freshly prepared, frozen or dried for convenient storage.

To conduct susceptibility tests the above described devices are inoculated with a standardized microbiological inoculum and incubated until visible growth appears. This typically takes 15– 24 hours. Generally, microbial growth in either a liquid medium or on the surface of a solid support medium is determined by direct visual recognition or by turbidometric measurements. The endpoint of susceptibility tests is defined as the lowest concentration of an antimicrobial agent in which growth, when compared to that of the growth compartment, appears to be inhibited.

Commonly used susceptibility tests require 15–24 hours of incubation prior to the availability of results. Earlier receipt by the physician of accurate antimicrobial agent susceptibility information would result in better patient treatment. A number of methods have been published to obtain earlier susceptibility determinations. They may be divided into measurement of bacterial mass described in U.S. Pat. Nos. 4,236,211 (Pfizer), 3,832,532 (Pfizer), G.B. Patent No. 1,554,134 (Pfizer), and indirect estimation of bacterial mass by measurement of enzymatic activity described in U.S. Pat. No. 4,242,447 (Bio Research), fluorogenic measurement of phosphate, U.S. Pat. No. 3,509,026 (Litton Systems Inc.), fluorogenic measurement of phosphotase, FR 2,504,679, use of methylumbelliferyl derivatives, EP 0,091,837B and in articles describing the use of amidocoumarin derivatives for antibiotic susceptibility testing by M. R. Mateo, et al., Abstract Annual Meeting, American Society for Microbiology, 1980, C201, P. 308 and the measurement of metabolic activity by reduction of tetrazolium in microdilution panels by T. Urban and C. Jarstrand, J. Antimicro. Chemo (1981) 8, 363–369. All the following are about the use of a mixture of fluorogenic substrates: Nolte et al., J. Clin. Microbio. (1988) 26, 1079–1084, Staneck et al., J. Clin. Microbiol. (1985), 187–191, Doern et al., J. Clin. Micro. (1987), 1481–1485, and Staneck et al., J. Clin. Micro. (1988) v. 26 1–7.

One particular method is the Sensititre™ system which has an instrument capable of automatically reading antimicrobial susceptibility microdilution trays. In this procedure, microbial growth is determined by the measurement of fluorescence produced by bacterial enzymatic action on fluorogenic substrates. The fluorescence signals are interpreted by the instrument and converted to MIC's. Staneck, (1985) Supra at 187. The Sensititre™ method involves the use of a fluorogenic substrate cocktail to detect the minimal inhibitory concentration for Gram positive and Gram negative bacteria based on a single measurement within five hours of the addition of the hydrolysable fluorogenic substrates to the inoculum. It is disclosed that the fluorogenic substrates for this group of bacteria are selected from 7-(N)-(aminoacyl)-7-amido-4-methylcoumarin, 4-methylumbelliferyl nonanoate, 4-methylumbelliferyl phosphate. EP 0,091,837B.

Single measurement methods to predict or determine minimal inhibitory concentration using fluorogenic substrates, however, have been found to be unreliable. In order to determine accurate minimal inhibitory concentrations sufficient growth and utilization of the substrate must occur. A single measurement precludes the accurate determination of a minimal inhibitory concentration under optimum conditions because different bacterial species may obtain sufficient growth to determine minimal inhibitory concentrations at different times. A single early measurement may result in an inaccurate prediction of a minimal inhibitory concentration because of insufficient expression of resistance. A single late measurement may result in an inaccurate estimation of enzymatic activity in the antimicrobial agent containing compartment in relation to that of the growth compartment. After a certain fluorescence level is reached, the photometric detection system is unable to accurately determine fluorescence. Consequently, a need exists to develop a system to accurately predict minimal inhibitory concentrations for a wide range of Gram positive organisms using fluorogenic substrates in one standardized test system.

SUMMARY OF THE INVENTION

The present invention involves a method for determining antimicrobial susceptibility of a wide variety of Gram positive organisms comprising: a) suspending and homogeneously mixing a sufficient number of morphologically similar colonies of the Gram positive organism in an aqueous suspending medium to prepare an inoculum having a turbidity equivalent to at least 0.5 McFarland Barium Sulfate, turbidity standard; b) diluting said inoculum in a sufficient amount of a growth supporting medium to achieve a nominal concentration of about $2 \times 10^6$ colony forming units/ml; c) combining a portion of said inoculum with a sufficient amount of fluorogenic substrates consisting of: leucine-7-amido-4-methylcoumarin, phenylalanine-7-amido-4-methylcoumarin and 4-methylumbelliferyl phosphate and a predetermined amount of an antimicrobial agent to form a mixture; d) repeatedly monitoring fluorescence intensity of said mixture between about 3½ to 15 hours after step 1(c) to detect a given increase in fluorescence intensity and e) comparing said detected fluorescence intensity with changes in fluorescence intensity of a control or controls to determine susceptibility to antimicrobial agents of said Gram positive organisms. A kit to conduct the above described method comprised of control, growth control, and antimicrobial agents in individualized compartments: said control compartments containing buffer, said growth control compartments containing buffer and fluorogenic concentrate, and said antimicrobial agent compartment containing buffer, antimicrobial agent and fluorogenic concentrate. All kit biochemical components are in a stable format, such as in the dehydrated state.

The invention differs from the procedure previously described for Gram positive bacteria used by Sensititre™ EP #0,091837 in three important aspects. First, the mixture of fluorogenic enzyme substrates; secondly, in the scope of organisms covered; and thirdly, in the repeated measurement of fluorescence.

In the Sensititre™ procedure the substrates mixture consists of alanyl-7-amido-4-methylcoumarin, 4-methylumebelliferyl phosphate and 4-methylumbelliferyl nonanoate. The last compound is difficult to redissolve evenly after dehydration. Moreover, a special procedure of drying the substrate mixture on a solid carrier in combination with an emulsifying agent was the preferred method in the EP #0,09187 description. Removal of this compound from the mixture allows easy preparation and aliquoting of the fluorogenic substrate mixture. In the current invention phenylalanine-7-amido-4-methylcoumarin and leucine-7-amido-4-methylcoumarin provide a superior mixture to that described before because it removes the need for an emulsifying agent during drying and the need of drying the fluorogenic enzyme substrates on a solid carrier. The current fluorogenic substrate mixture also allows for testing of a larger range of Gram positive species than previously described. Additionally, the use of the autoSCAN®-W/A allows monitoring of growth for between 3½ and 15 hours, determination of minimum inhibitory concentration occurring only when sufficient growth has been achieved. This ensures that the minimum inhibitory concentration determinations of each isolate is determined at the optimal time.

DETAILED DESCRIPTION

The invention combines three fluorogenic compounds to facilitate the detection of growth of the majority of clinically significant Gram positive organisms, staphylococci, streptococci, enterococci, and listeriae from between about 3½–15 hours. The combination of the three compounds is added to the growth control and to every concentration of the antimicrobial agents compartments. Growth of the organism is detected by an increase in fluorescence units.

As the organism grows, enzymes are produced which hydrolyze the fluorogenic compound(s), thus releasing the fluorophore, which, when excited by light in the 340–370 nm range, fluoresces in the 440–470 nm range. If the organism does not grow, the fluorophore part is not released from the compound, and there is no increase in fluorescence at the selected wavelength. After the organism has grown for between 3½–15 hour, the amount of fluorescence in the individual concentrations of the antimicrobial agents can be compared to the amount of fluorescence in the growth control, and the minimal inhibitory concentrations of each antimicrobial agent can be determined.

The advantage of utilizing a combination of fluorogenic compounds to detect growth, is the rapidity with which growth and consequently minimal inhibitory concentrations can be determined. Conventional minimal inhibitory concentration determinations, which rely on turbidity, require 15–24 hours of incubation prior to reading. Using a combination of certain compounds allows one to determine minimum inhibitory concentrations for the majority of Gram positive organisms, however, within 3½–15 hours.

Several combinations of fluorogenic compounds were tested and this combination detected growth of most species of Gram positive organisms. The compounds are leucine-7-amido-4-methylcoumarin, phenylalanine-7-amido-4-methylcoumarin, and 4-methylumbelliferyl phosphate. This combination detected the majority of clinically relevant species of staphylococci, streptococci, enterococci, and listeriae. See TABLE 1.

TABLE 1

| Staphylococcus aureus | S.cohnii | S.epidermidis |
|---|---|---|
| S.haemolyticus | S.hominis | S.hyicus hyicus |
| S.intermedius | S.lentus | S.saprophyticus |
| S.sciuri | S.similans | S.xylosus |
| S.kloosii | S.caseolyticus | S.chromogenes |
| S.carnosus | S.caprae | S.gallinarum |
| Streptococcus pyogenes (Group A) | St.equi/equisimilis | St.zooepidemicus |
| | St.bovis II | St.equinus |
| St.agalactiae (Group B) | St.sanguis I | St.sanguis II |
| St.bovis I | St.constellatus/milleri | St.morbillorum |
| St.mutans | St.mitis | Enterococcus |
| St.anginosus/milleri | St.pneumoniae | faecalis |
| St.intermedius/milleri | Ec.durans | Ec.avium |
| St.salivarius | | |
| Ec.faecium | | |
| Listeria monocytogenes. | | |

In particular, in this assay as the organism grows it metabolizes one, two, or all three components of the fluorogenic concentrate. Metabolic activity results in the release of fluorophores, amino-4-methylcoumarin and/or 4-methylumbelliferone which, when excited by light in the 340–370 nm range, emit light (fluoresce) in the 440–470 nm range. As the organism multiplies, the amount of fluorescence increases. The amount of fluorescence in each concentration of the antimicrobial agents is compared to the amount of fluorescence in the growth control. Using a mathematical model based on discriminate functional analysis, the minimum inhibitory concentration of each antimicrobial agent, for the organism tested, can be determined. Utilization of a discriminant function analysis model in microbiological pattern recognition is described in S. Bascomb, Computers in Taxonomy and Systematics, p. 65–102 In T. N. Bryant and J. W. T. Wimpenny (Ed.), Computers in Microbiology, a Practical Approach (IRL Press, Oxford). In an alternative embodiment the minimal inhibitory concentration for each antimicrobial agent for the organism tested can be determined by a break point or threshold method or by linear regression analysis. J. McKie, et al., Antimicrobial Agents and Chemotherapy (1980) v. 17, 813–823.

Generally, the invention involves making a stock solution containing the three fluorogenic compounds: leucine-7- amido-4-methylcoumarin (0.1M), phenylalanine-7-amido-4-methylcoumarin (0.05M) and 4-methylumbelliferyl phosphate (0.25M); dissolving the compounds in dimethylformamide; b) making the diluent which is HEPES buffer, 0.01M, pH 7.0 or a similar buffer. The antimicrobial agents are diluted in 0.01M buffer; and the fluorogenic concentrate (2 ml/L) is added to the growth control, which contains only buffer, and to each concentration of the antimicrobial agents. Additionally, a control which contains only buffer is used in this assay. The final concentration of the fluorogenic components per compartment are 0.2 mM leucine-7-amido- 4-methylcoumarin, 0.1 mM phenylalanine-7-amido-4-methylcoumarin, and 0.5 mM methylumbelliferyl phosphate. These concentrations were selected to assure optimum enzyme activity throughout the growth period. One hundred fifteen microliters of each of said solutions are dispensed into individual compartments of a microdilution panel. The panels are dehydrated and packaged in foil wrapping with a packet of desiccant. This package is stored at 2°–8° C.

The antimicrobial agents include: Amoxicillin/K, Clavulanate (Aug), Ampicillin (am), Ampicillin/Sulbactam (A/S), Cefamandole (Cfm), Cefazolin (Cfz), Cefotaxime (Cft), Ceftriaxone (Cax), Cefuroxime (Crm), Cephalotin (Cf), Chloramphenicol (C), Ciprofloxacin (Cp), Clindamycin (Cd), Erythromycin (E), Gentamicin (Gm), Gentamicin Synergy Screen (GmS) Imipenem (Imp), Nitrofurantoin (Fd), Norfloxacin (Nx), Oxacillin (Ox), Penicillin (P), Rifampin (Rif), Streptomycin Synergy Screen (Sts) (high concentration streptomycin in well. The screen determines that a combination of streptomycin and another antibiotic will be affective.), Tetracycline (Te), Trimethoprim (T), Trimethoprim Sulfamethoxazole (T/S) and Vancomycin (Va).

Generally, the test procedure involves making a suspension of a Gram positive organism, which is equivalent to a 0.5 McFarland barium sulfate turbidity standard in a saline pluronic broth. Three hundred microliters of the suspension is diluted into 25 milliliters of the inoculum broth. The suspension is mixed. The dried panels are rehydrated with 115 microliters of the inoculum broth per suspension. Rapid Pos® Inoculum Broth (Baxter MicroScan). The panels are incubated at 35°±1° C. in a non-$CO_2$ incubator. The panels are read in a fluorometer at designated times. MicroScan has an autoScan® W/A (Baxter MicroScan) instrument which incubates and reads the panels automatically at designated times.

The following table shows the distribution of reagents and inoculum in the growth control and antimicrobial agent wells.

TABLE 2

|  | Growth Well | Control Well | Antimicrobial Agent Well |
| --- | --- | --- | --- |
| Inoculum | + | + | + |
| Growth Medium | + | + | + |
| Fluorogenic Substrates | + | − | + |
| Antimicrobial Agent | − | − | + |
| Growth | + | + | −/+ |
| Increase in Fluorescence | + | − | −/+ |

Using the above described assay, the majority of clinically significant Gram positive organisms, See TABLE 3, were tested to determine the efficacy of this test to determine the minimal inhibitory concentration of certain antimicrobial agents.

TABLE 3

| ORGANISMS TESTED FOR EFFICACY | |
| --- | --- |
| Organisms: | Number Tested |
| *Staphylococcus aureus* | 187 |
| Methicillin - Susceptible | (92) |
| Methicillin - Resistant | (95) |
| Coagulase - negative Staphylococci | 144 |
| *Staphylococcus epidermidis* | (49) |
| *Staphylococcus saprophyticus* | (15) |
| Other coagulase - negative Staphylococci | (80) |
| Group D Streptococci (Enterococci) | 110 |
| Beta Hemolytic Streptococci (*St.pyogenes* and *St.agalactiae*) | 77 |
| Viridans Streptococci | 29 |
| *Streptococcus pneumoniae* | 32 |
| *Listeria monocytogenes* | 16 |

For the organisms shown in Table 3, the following efficacy of this test was reported for the antimicrobial agents listed in Table 4. A 95.9% agreement with a reference minimal inhibitory concentration determination was obtained.

TABLE 4

| EFFICACY SUMMARY REPORT | | | | | | |
| --- | --- | --- | --- | --- | --- | --- |
| ANTIMICROBIC | TOTAL | +/−1 DILUTION | * VMJ | ** MAJ | *** MIN | AGREEMENT |
| Ampicillin | 592 | 571 | 6 | 4 | 4 | 96% |
| Ampicillin/Sulbactam | 593 | 577 | 0 | 3 | 3 | 97% |
| Amoxicillin/ K. Clavulanate | 591 | 572 | 11 | 0 | 0 | 97% |
| Clindaimycin | 593 | 540 | 19 | 14 | 20 | 91% |
| Gentamicin | 345 | 327 | 7 | 6 | 4 | 95% |
| Imipenem | 593 | 558 | 9 | 3 | 6 | 94% |
| Norfloxacin | 593 | 585 | 3 | 3 | 0 | 99% |
| Oxacillin | 319 | 289 | 5 | 15 | 0 | 91% |
| Penicillin | 593 | 553 | 19 | 6 | 5 | 93% |
| Trimethoprim | 440 | 430 | 7 | 3 | 0 | 98% |
| Trimethoprim/ Sulfamethoxazole | 440 | 428 | 1 | 9 | 0 | 97% |
| Vancomycin | 593 | 592 | 0 | 0 | 0 | 100% |

TABLE 4-continued

EFFICACY SUMMARY REPORT

| ANTIMICROBIC | TOTAL | +/−1 DILUTION | * VMJ | ** MAJ | *** MIN | AGREEMENT |
|---|---|---|---|---|---|---|
| Cefazolin | 593 | 547 | 10 | 16 | 6 | 92% |
| Ceftriaxone | 594 | 555 | 5 | 7 | 26 | 93% |
| Cefuroxime | 595 | 552 | 10 | 10 | 10 | 93% |
| Cefotaxime | 595 | 543 | 11 | 20 | 16 | 91% |
| Chloramphenicol | 595 | 568 | 3 | 1 | 0 | 95% |
| Cefamandole | 595 | 568 | 3 | 3 | 4 | 95% |
| Cephalothin | 595 | 589 | 4 | 2 | 0 | 99% |
| Ciprofloxacin | 595 | 588 | 0 | 1 | 6 | 99% |
| Erythromycin | 595 | 566 | 11 | 4 | 13 | 95% |
| Nitrofurantoin | 595 | 584 | 0 | 11 | 0 | 98% |
| Rifampin | 595 | 586 | 5 | 4 | 0 | 98% |
| Tetracycline | 595 | 566 | 10 | 4 | 5 | 95% |
| Streptomycin Synergy Screen | 594 | 582 | 4 | 8 | 0 | 98% |
| Gentamicin Synergy Screen | 593 | 587 | 2 | 4 | 0 | 99% |
| TOTAL | 14,609 | 14,003 | 165 | 161 | 128 | |
| PERCENT | | 95.9% | 1.1% | 1.1% | 0.9% | 95.9% |
| AGREEMENT (± dil) = 95.9% | | | | | | |

*VMJ — Very Major Error — A very major error occurred when the isolate was categorized as susceptible by the test method and as resistant by the reference method.
**MAJ — Major Error — A major error occurred when the isolate was categorized as resistant by the test method and as susceptible by the reference method.
***MIN — Minor Error — A minor error occurred when the isolate was categorized as moderately susceptible by one method and as susceptible or resistant by the other method.

Examples of the invention are given below:

EXAMPLE 1

A primary inoculum suspension of a bacterial isolate in saline-pluronic, equivalent to a 0.5 McFarland turbidity standard is prepared. The final inoculum suspension is prepared by diluting a 0.3 ml aliquot of the primary suspension in 25 ml of Rapid Pos Inoculum Broth (B1015-14, Baxter Diagnostics Inc., MicroScan Division, West Sacramento, Calif.). A 115 µl of the final inoculum is added to the growth compartment which contains dried material of fluorogenic enzyme substrates equivalent to 0.023 mM leucine-7-amido-4-methylcoumarin, 0.012 mM phenylalanine-7-amido-4-methylcoumarin and 0.058 mM methylumbelliferyl phosphate and 1.15 mM HEPES buffer at pH 7.0. The final inoculum is also added to a number of compartments containing dried material identical to that in the growth well and different concentrations of an antimicrobial agent. An aliquot of the final inoculum is also added to a compartment, containing only dried HEPES buffer, acting as a control. The inoculated multicompartment device (panel) is inserted in the autoSCAN®-W/A. The fluorescence of each compartment is measured at predetermined times and a Growth Index is calculated by dividing the fluorescence of the growth compartment by that of the negative control compartment. See Table 5.

TABLE 5

| Growth Factor | $^{FL}$growth well / $^{FL}$control well |
|---|---|
| $\%^{FL}$drug = | ($^{FL}$drug − $^{FL}$control) / ($^{FL}$growth − $^{FL}$control) |

If the value of the Growth Index is equal to or exceeds a specified value, the Minimum Inhibitory Concentration for every antimicrobial agent present in the multicompartment device is calculated. Otherwise the device is returned to its position and measured again at the next read time. The read times in this example are 3.5, 4.5, 5.5, 7.0, 8.0, 11.0, and 15.0 hours. For calculation of minimum inhibitory concentration, the percent fluorescence of compartments containing the different concentrations of the antimicrobial agent is calculated by subtracting from each compartment the fluorescence of the control well and dividing it by the delta fluorescence of the growth compartment, obtained by subtracting the fluorescence of the negative control compartment from the fluorescence of the growth compartment. The minimum inhibitory concentration is calculated using a mathematical model specific for each concentration range of the antimicrobial agent. Using a mathematical model based on discriminate functional analysis, the minimum inhibitory concentration of each antimicrobial agent, for the organism tested, can be determined. Utilization of a discriminate function analysis model in microbiological pattern recognition is described in S. Bascomb, Computers in Taxonomy and Systematics, p. 65–102 In T. N. Bryant and J. W. T. Wimpenny (Ed.), Computers in Microbiology, a Practical Approach (IRL Press, Oxford). In an alternative embodiment the minimum inhibitory concentration for each antimicrobial agent for the organism tested can be determined by a breakpoint or threshold method or linear regression analysis. J. McKie, et al., Antimicrobial Agents and Chemotherapy (1980) v. 17, 813–823.

In Example 1, the growth of Enterococcus faecalis in wells containing specified amounts of antimicrobial agents is estimated by measurement of fluorescence. In Table 6, the percent fluorescence at different concentrations of antimicrobial agents is reported. For example, 0.12, 0.25, 0.5, 1, 2, 4 and 8 µg/mL of ampicillin (Am) were present in the microdilution wells.

The numbers 105, 105, 67, 7, 6, 5, 6 are percent fluorescence values as calculated in Table 5. These figures are used to determine susceptibility according to the methods discussed on pages 12 and 13.

TABLE 6

Minimum Inhibitory Concentration Determination

| | | | | | |
|---|---|---|---|---|---|
| 5 | 95 | 105 | 105 | 67 | 7 |
| Sts | GmS | .12Am | .25Am | .5Am | 1Am |
| 6 | 5 | 6 | 99 | 104 | 105 |
| 2Am | 4Am | 8Am | .03P | .06P | .12P |
| 105 | 105 | 93 | 12 | 7 | 7 |
| 25P | .5P | 1P | 2P | 4P | 8P |
| 104 | 105 | 3928 | 103 | 98 | 100 |
| 8Cfm | 16Cfm | C | .250x | .50x | 10x |
| 99 | 95 | 90 | 91 | 85 | 79 |
| 20x | 40x | 80x | .5Te | 1Te | 2Te |
| 71 | 62 | 37 | 105 | 102 | 104 |
| 4Te | 8Te | 128Te | 2Cfz | 4Cfz | 8Cfz |
| 100 | 103 | 7 | 61369 | 47805 | 85 |
| 16Cfz | 8Cf | 16Cf | G | 0xG | 2Crm |
| 39 | 15 | 10 | 10 | 8 | 8 |
| 4Crm | 8Crm | 16Crm | 4Cft | 8Cft | 16Cft |
| 7 | 15 | 9 | 8 | 7 | 65 |
| 32Cft | 4Cax | 8Cax | 16Cax | 32Cax | 1Imp |
| 5 | 5 | 5 | 105 | 99 | 95 |
| 2Imp | 4Imp | 8Imp | 1Gm | 2Gm | 4Gm |
| 93 | 93 | 59 | 9 | 5 | 5 |
| 6Gm | 8Gm | .25E | .5E | 1E | 2E |
| 4 | 58 | 21 | 5 | 5 | 5 |
| 4E | 1Rif | 2Rif | 2Va | 4Va | 8Va |
| 2 | 88 | 83 | 75 | 71 | 5 |
| 16Va | .25Cd | 5Cd | 1Cd | 2Cd | 8A/S |
| 5 | 84 | 94 | 6 | 6 | 6 |
| 16A/S | 2T/S | 8T/S | 1Cp | 2Cp | 4Cp |
| 6 | 6 | 6 | 5 | 86 | 21 |
| 4Nxn | 8Nxn | 2Aug | 4Aug | 32Fd | 46Fd |
| 9 | 6 | 4 | | | |
| 4C | 8C | 16C | | | |

G = Growth Compartment
C = Control Compartment

TABLE 7

| PL | PS | Ox | Cfz |
|---|---|---|---|
| N/R | N/R | N/R | >16 |
| Cft | Gm | Va | Cp |
| >4 | N/R | <2 | <1 |
| NxN | AmO | AmL | AmS |
| <4 | 0.5 | N/R | N/R |
| Cf | Cd | E | Aug |
| 16 | >2 | 4 | <2 |
| Te | Fd | Crm | Imp |
| 128 | <32 | >16 | 4 |
| A/S | Cfm | C | Rif |
| <8 | >16 | <4 | 2 |
| T/X | Sts | | |
| >8 | 5 | | |

In Table 7, the minimum inhibitory concentration for Example 1 are reported. For the antimicrobial agent, cephalothin, the organism was found to be susceptible at a concentration at 16 µg/mL. For ampicillin/sulbactans susceptibility was observed at less than 8 µg/mL while the organism was resistant to trimethoprim/sulfamethoxazole at greater than 8 µg/mL. The organism was susceptible to norfloxacin, cefotaxime and chloramphenic at less than 4 µg/mL, while susceptiblity at 4 µg/mL was observed of Imipenem and erythromycin. Additionally, the organism was found to be susceptible at less than 2 µg/mL of vancomycin and amoxicillin/K.Clavalanate and at 2 µg/mL of rifampin. The organism was resistant at greater than 2 µg/mL of clindamycin. The organism was found to be susceptible at less than 1 µg/mL of ciprofloxacin. The organism was found to be susceptible to 0.5 µg/mL of ampicillin. The organism was found to be susceptible at 128 µg/mL to tetracycline. The organism was found to be susceptible to less than 32 µg/mL, of nitrofurantoine. The organism was found to be resistant at greater than 16 µg/mL for cefazolin, cefuroxime, and cefamandole. Additionally, it was determined that this organism was susceptible to a Streptomycin Synergy Screen.

Variants or equivalents: one alternative would be to use other combinations of fluorogenic compounds. The combination described above worked the best and detected the greatest number of Gram positive organisms. Other compounds tested were alanine- 7-amido-4-methylcoumarin and methionine-7-amido-4 -methylcoumarin. The individual concentrations of the compounds or the ratio of compounds in the mixture could be varied.

We claim:

1. A method for determining susceptibility to antimicrobial agents of clinically significant Gram positive organisms wherein the organisms are selected from the group consisting of Staphylococci, Streptococci, Enterococci, and Listeria, the method comprising:
   a. suspending and homogeneously mixing a sufficient number of morphologically similar colonies of Gram positive organisms in an aqueous suspending medium to prepare an inoculum having a turbidity equivalent to at least 0.5 McFarland barium sulfate turbidity standard;
   b. diluting said inoculum in growth supporting medium;
   c. combining a sufficient amount of said diluted inoculum/growth supporting medium with a sufficient amount of a fluorogenic substrate combination consisting essentially of leucine-7-amido-4-methylcoumarin, phenylalanine-7-amido-4-methylcoumarin and 4 -methylumbelliferyl phosphate, and a predetermined amount of an antimicrobial agent to form a mixture wherein the amount of the diluted inoculum/growth supporting medium and the amount of the fluorogenic substrate combination are sufficient to induce a change in fluorescence in the absence of the antimicrobial agent;
   d. monitoring fluorescence intensity of said mixture for a time period of between about 3½ and 15 hours after step (c) to detect a given increase in fluorescence intensity; and
   e. comparing said detected fluorescence intensity with changes in fluorescence intensity of a control to determine susceptibility to antimicrobial agents of said Gram positive organisms.

2. The method of claim 1 where said control consists of a growth control and a buffer control wherein said growth control consists essentially of buffer and said fluorogenic substrate combination.

3. The method of claim 1 wherein said Gram positive organisms are selected from the groups consisting of Staphylococcus aureus, S.cohnii, S.epidermidis, S.haemolyticus, S.hominis, S.hyicus-hyicus, S.intermedius, S.lentus, S.saprophyticus, S.sciuri, S.similans, S.xylosus, S.kloosii, S.caseolyticus, S.chromogenes, S.carnosus, S.caprae, and S.gallinarum, Streptococcus pyogenes (Group A), St.agalactiae (Group B), St.equi/equismilis, St.zooepidemicus, St.bovis I, St.bovis II, St.equinus, St.mutans, St.sanguis I, St.sanguis II, St.anginosus/milleri, St.constellatus/milleri, St.intermedius/milleri, St.mitis, St.morbillorum, St.salivarius, St.pneumoniae, Enterococcus faecalis, Ec.faecium, Ec.durans, Ec.avium, and Listeriae monocytogenes.

4. The method of claim 1 wherein said antimicrobial agent is selected from the groups consisting of Amoxicillin/K Clavulanate, Ampicillin, Ampicillin/Sulbactam, Cefamandole, Cefazolin, Cefotaxime, Ceftriaxone, Cefuroxime, Cephalothin, Chloramphenicol, Ciprofloxacin, Clindamycin, Erythromycin, Gentamicin, Gentamicin Synergy Screen, Imipenem, Nitrofurantoin, Norfloxacin, Oxacillin, Penicillin, Rifampin, Streptomycin Synergy Screen, Tetracycline, Trimethoprim, Trimethoprim/Sulfamethoxazole and Vancomycin.

5. A kit to conduct the method of claim 1 comprising individual compartments of control, growth control, and antimicrobial agents, said control compartments containing buffer, said growth control compartments containing buffer and a fluorogenic substrate combination and said antimicrobial agent compartments containing buffer, antimicrobial agent and fluorogenic substrate combination wherein the fluorogenic substrate combination consists essentially of leucine-7-amido-4-methylcoumarin, phenylalanine-7-amido-4-methylcoumarin and 4-methylumbelliferyl phosphate.

6. The kit of claim 5 wherein said fluorogenic substrate combination is concentrated.

7. The kit of claim 5 wherein said buffer antimicrobial agent and fluorogenic substrate combination are dehydrated.

8. A method for determining susceptibility to antimicrobial agents of clinically significant Gram positive organisms wherein the organisms are selected from the group consisting of Staphylococci, Streptococci, Enterococci, and Listeria, the method comprising:

a. suspending and homogeneously mixing a sufficient number of morphologically similar colonies of Gram positive organisms in an aqueous suspending medium to prepare an inoculum having a turbidity equivalent to at least 0.5 McFarland barium sulfate turbidity standard;

b. diluting said inoculum in growth supporting medium;

c. combining a sufficient amount of said diluted inoculum/growth supporting medium with a sufficient amount of a fluorogenic substrate combination consisting essentially of leucine-7-amido-4-methylcoumarin, phenylalanine-7-amido-4-methylcoumarin and 4-methylumbelliferyl phosphate, a predetermined amount of an antimicrobial agent and a sufficient amount of buffer to stabilize said fluorogenic substrate in individual microwell dilution compartments to form antimicrobial agents wells;

d. combining a sufficient amount of said diluted inoculum/growth supporting medium with a sufficient amount of fluorogenic substrate combination consisting essentially of leucine-7-amido-4-methylcoumarin, phenylalanine-7-amido-4-methylcoumarin and 4-methylumbelliferyl phosphate, and a sufficient amount of buffer to stabilize said fluorogenic substrate in individual microwell dilution compartments to form growth wells;

e. combining a sufficient amount of said diluted inoculum/growth supporting medium with a sufficient amount of buffer in individual microwell dilution compartments to form control wells;

f. repeatedly monitoring fluorescence intensity of said wells for a time period between 3½ to 15 hours after steps (c), (d) and (e); and g. comparing said detected fluorescence intensities of said antimicrobial agent wells with said growth wells and control wells to determine susceptibility to antimicrobial agent of said Gram positive organisms;

wherein the amount of the diluted inoculum/growth supporting medium and the amount of the fluorogenic substrate combination are sufficient to induce a change in fluorescence in the absence of the antimicrobial agent.

9. The method of claim 8 wherein said Gram positive organisms are selected from the class consisting of *Staphylococcus aureus, S.cohnii, S.epidermidis, S.haemolyticus, S.hominis, S.hyicus-hyicus, S.intermedius, S.lentus, S.saprophyticus, S.sciuri, S.similans, S.xylosus, S.kloosii, S.caseolyticus, S.chromogenes, S.carnosus, S.caprae, and S.gallinarum, Streptococcus pyogenes* (Group A), *St.agalactiae* (Group B), *St.equi/equismilis, St.zooepidemicus, St.bovis* I, *St.bovis* II, *St.equinus, St.mutans, St.sanguis* I, *St.sanguis* II, *St.anginosus/milleri, St.constellatus/milleri, St.intermedius/milleri, St.mitis, St.morbillorum, St.salivarius, St.pneumoniae, Enterococcus faecalis, Ec.faecium, Ec.durans, Ec.avium, and Listeriae monocytogenes.*

10. The method of claim 8 wherein said antimicrobial agent is selected from the class consisting of Amoxicillin/K Clavulanate, Ampicillin, Ampicillin/Sulbactam, Cefamandole, Cefazolin, Cefotaxime, Ceftriaxone, Cefuroxime, Cephalothin, Chloramphenicol, Ciprofloxacin, Clindamycin, Erythromycin, Gentamicin, Gentamicin Synergy Screen, Imipenem, Nitrofurantoin, Norfloxacin, Oxacillin, Penicillin, Rifampin, Streptomycin Synergy Screen, Tetracycline, Trimethoprim, Trimethoprim/Sulfamethoxazole and Vancomycin.

* * * * *